United States Patent
Zuluaga et al.

(10) Patent No.: US 7,310,357 B2
(45) Date of Patent: Dec. 18, 2007

(54) PROVIDING LOW-COHERENCE LIGHT (75) Inventors: Andres Zuluaga, Boston, MA (US); Jay Caplan, Belmont, MA (US)

(73) Assignee: InfraReDx, Inc., Burlington, MA (US)

( * ) Notice: Subject to any disclaimer, the term of this patent is extended or adjusted under 35 U.S.C. 154(b) by 525 days.

(21) Appl. No.: 11/071,120

(22) Filed: Mar. 2, 2005

(65) Prior Publication Data
US 2006/0198400 A1 Sep. 7, 2006

(51) Int. Cl.
*H01S 3/10* (2006.01)
*H01S 3/08* (2006.01)

(52) U.S. Cl. .............................. 372/9; 372/92; 372/99

(58) Field of Classification Search .................. 372/9, 372/92, 99
See application file for complete search history.

(56) References Cited

U.S. PATENT DOCUMENTS

| | | | |
|---|---|---|---|
| 5,022,042 A | 6/1991 | Bradley | |
| 5,077,747 A | 12/1991 | Hemmer et al. | |
| 5,428,635 A | 6/1995 | Zhiglinsky et al. | |
| 6,081,539 A | 6/2000 | Mattori et al. | |
| 6,791,739 B2 | 9/2004 | Ramanujan et al. | |
| 2004/0064022 A1 | 4/2004 | Korn | |
| 2004/0109478 A1 | 6/2004 | Korn | |

OTHER PUBLICATIONS

Gregor Hackenbroich. "Statistical Theory of Multimode Random Lasers." Fachbereich Physik, Universität Duisburg-Essen, Mar. 8, 2004. 1-4.

C. Serrat et al. "Dynamics and Coherence of a Multimode Semiconductor Laser with Optical Feedback in an Intermediate-Length External-Cavity Regime." Physical Review, A vol. 68 053804 (2003) 1-7.

A. Uchida et al. "Chaotic Antiphase Dynamics and Synchronization in Multimode Semiconductor Lasers." Physical Review, A, vol. 64, 023801, 1-6.

*Primary Examiner*—Armando Rodriguez
(74) *Attorney, Agent, or Firm*—Fish & Richardson P.C.

(57) ABSTRACT

The invention features an apparatus and an associated method for illuminating a target area. The apparatus includes reflectors defining a first optical cavity. The first optical cavity defines a first set of longitudinal modes. The apparatus includes a first gain medium defining a first gain band. The first gain medium is configured to cause a plurality of the longitudinal modes of the first set to oscillate over an oscillation band within the first gain band when the first gain medium is pumped at an operative level. The apparatus includes a first optical waveguide positioned within the first optical cavity. The first optical waveguide has a length selected to cause a temporal coherence length of light emitted from the first optical cavity to be shorter than a scattering distance associated with the target area.

24 Claims, 5 Drawing Sheets

PROVIDING LOW-COHERENCE LIGHT

BACKGROUND

The invention relates to providing low-coherence light.

Sources of coherent light typically include an optical cavity that includes a gain medium. Gain media can include media that provide gain through "population inversion" such as a semiconductor gain medium of a solid-state laser, or other types of media such as a nonlinear optical medium that provides gain through nonlinear conversion.

Tunable sources of coherent light are applicable to a number of diagnostic and therapeutic medical applications. Optical coherence tomography is used to provide spatial resolution, enabling the imaging of internal structures. Spectroscopy is used to characterize the composition of structures, enabling the diagnosis of medical conditions, by differentiating between cancerous, dysplastic, and normal cellular structures.

In some cases the coherence of the light can lead to constructive and/or destructive interference over a transverse profile of a beam when the beam travels through a scattering medium (e.g., blood) to a sample. This "speckle effect" can lead to noise in a detected image or spectral signal.

Speckle can also be caused in other contexts including, for example, after a beam traveling through air scatters from a rough surface, such as in a laser projector illuminating a rough screen or wall.

Some approaches to reducing speckle in various contexts include reducing the temporal coherence of the light by broadening the linewidth of the source, splitting the illuminating wavefront into beamlets and delaying them relative to each other by longer than the coherence time of the source, or vibrating the sample to average out fluctuations.

SUMMARY

The invention is based, at least in part, on the recognition that speckle at a target area can be reduced by increasing the optical cavity length of a light source to cause the temporal coherence length of the emitted light to be shorter than a scattering distance associated with the target area, where the scattering distance characterizes an average distance between scattering events. For example, in the case of a light source illuminating a target area through a scattering medium, the scattering distance is a mean free path within the scattering medium. In the case of a light source scattering from a rough surface of the target area, the scattering distance is a transverse roughness of the surface. Any of a variety of optical cavity configurations can be adapted to include an optical waveguide, such as an optical fiber, that can be made long enough to reduce the temporal coherence length without causing the cavity to be unstable.

In one aspect, the invention features an apparatus and an associated method for illuminating a target area. The apparatus includes reflectors defining a first optical cavity. The first optical cavity defines a first set of longitudinal modes. The apparatus includes a first gain medium defining a first gain band. The first gain medium is configured to cause a plurality of the longitudinal modes of the first set to oscillate over an oscillation band within the first gain band when the first gain medium is pumped at an operative level. The apparatus includes a first optical waveguide positioned within the first optical cavity. The first optical waveguide has a length selected to cause a temporal coherence length of light emitted from the first optical cavity to be shorter than a scattering distance associated with the target area.

Embodiments of the invention can include one or more of the following features.

The scattering distance is a mean free path within the scattering medium adjacent to the target area, or a transverse roughness of the target area.

The apparatus includes a signal normalization system configured to detect intensity fluctuations in light emitted from the first optical cavity and to normalize, at least in part on the basis of the detected intensity fluctuations, a signal derived from light scattered from the target area.

The signal normalization system includes a first detector positioned to detect a portion of the light emitted from the first optical cavity, and a second detector positioned to detect the light scattered from the target area.

The signal normalization system also includes a synchronizer configured to enforce a phase relationship between a signal generated by the first detector and a signal generated by the second detector.

The first gain medium includes a semiconductor material or a doped crystal.

The apparatus also includes a tuning element, positioned within the first optical cavity, that causes the oscillation band to shift relative to the gain band in response to a control signal.

The tuning element is a diffraction grating, a stretchable fiber Bragg grating, a fiber on an electro-optic tuning element, a Fabry Perot filter, or a tilted dielectric stack mirror.

The apparatus also includes reflectors defining a second optical cavity. The second optical cavity defines a second set of longitudinal modes. A second gain medium defines a second gain band. The second gain medium is configured to cause a plurality of the longitudinal modes of the second set to oscillate over an oscillation band within the second gain band when the second gain medium is pumped at an operative level. The apparatus includes a coupling element configured to couple light from the first optical cavity with light from the second optical cavity.

The coupling element couples light from the first and second optical cavities inside at least one of the first and second optical cavities.

The coupling element couples light from the first and second optical cavities outside the first and second optical cavities.

The apparatus also includes a second optical waveguide positioned within the second optical cavity. The second optical waveguide has a length selected to cause a temporal coherence length of light emitted from the second optical cavity to be shorter than a scattering distance associated with the target area.

The apparatus also includes a catheter in optical communication with the first optical cavity. The catheter is configured to deliver light from the first optical cavity to the target area through the scattering medium and to collect scattered light from the target area.

The apparatus also includes a spectrum analyzer in optical communication with the catheter, the spectrum analyzer is configured to receive the scattered light.

A round-trip optical length of the first optical cavity is longer than 10 meters, 50 meters, 100 meters, or 500 meters.

The first optical cavity is configured according to a Littrow configuration.

The first optical cavity is configured according to a Littman-Metcalf configuration.

As used herein, "light" means optical radiation having any wavelength including, for example, infrared light, visible light, or ultraviolet light.

As used herein, "temporal coherence length" means a quantity $ct_c$ where c is the speed of light in a vacuum and $t_c$ is a coherence time.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will become apparent from the following description, and from the claims.

DESCRIPTION

1 System Overview

Figures 1A, 1B:
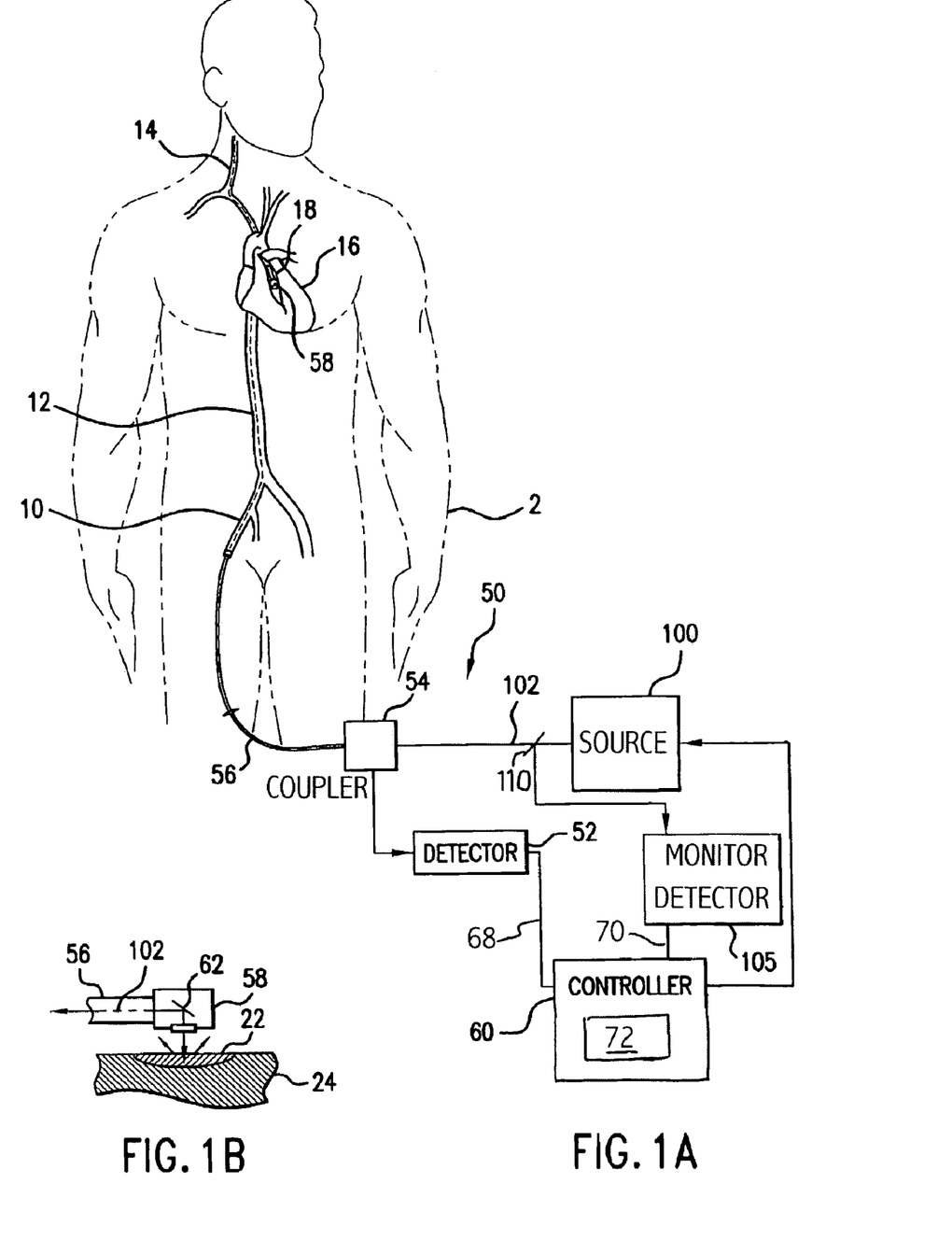
FIG. 1A is a schematic block diagram illustrating a spectroscopic catheter system.
FIG. 1B is a cross-sectional view of the distal end of the catheter system shown in FIG. 1A

Referring to FIG. 1, a spectroscopic catheter system 50 includes a light source 100 that provides light (e.g., infrared light, visible light, or ultraviolet light) for diagnostic and/or therapeutic treatment of a patient 2. The catheter system 50 includes a catheter 56 through which an optical fiber or optical fiber bundle extends. The catheter 56 is typically inserted into the patient 2 via a peripheral vessel, such as the femoral artery 10. The catheter head 58 is then moved to a desired target area, such as a coronary artery 18 of the heart 16 or the carotid artery 14. In this example, this is achieved by moving the catheter head 58 up through the aorta 12.

When at the desired site, an illuminating light 102 provided by the light source 100 is tuned to scan a spectral band of interest, such as a near infrared (NIR) spectral band. Scattered light from the target area is coupled into the optical fiber(s) of the catheter 56 to be transmitted to the catheter head 58.

With reference to FIG. 1B, illuminating light 102 transmitted by the optical fiber(s) and directed out of the head 58 by a fold mirror 62 impinges on a target area 22 of an artery wall 24. The catheter head 58 then collects scattered light from the target area 22. In some cases, light traveling between the catheter head 58 and the target area 22 travels through a scattering medium such as blood.

Returning to FIG. 1A, the scattered light is transmitted through the optical fiber(s) to a coupler 54. In some cases the scattered light travels through the same optical fiber(s) that delivers the illuminating light 102. In these cases, the coupler 54 includes a splitter (e.g., a circulator) to separate the illuminating light 102 and the scattered light. In other cases, the illuminating light 102 and the scattered light travel through separate optical fiber(s).

The coupler 54 directs the scattered light to a measurement detector 52, which can include one or multiple detectors (e.g., for direct intensity detection or phase-sensitive interferometric detection). The measurement detector 52 generates an electrical measurement signal 68 from which a control and analysis module 60 (or "controller" 60) obtains imaging and/or spectral information. The controller 60 can optionally incorporate or interface to any of a variety of modules to aid in analyzing the collected information, such as a spectrum analyzer.

A monitor detector 105 detects a portion of the illuminating light 102, provided by a beamsplitter 110, and provides an electrical monitor signal 70 indicative of intensity fluctuations in the illuminating light 102 to the controller 60. This monitor signal 70 is used in the signal normalization subsystem described below. The monitor detector 105 is optionally able to monitor other characteristics of the illuminating light 102, such as its spectrum.

The controller 60 controls the light source 100 by, for example, scanning the source spectrum to probe the NIR spectral response of the target area 22. Different implementations of the controller 60 and the source 100 use different approaches for scanning the source spectrum. In some implementations, the controller 60 tunes a source oscillation band over a source gain band, as described in more detail below. In other implementations, the controller 60 switches among multiple (tunable or non-tunable) optical cavities providing light at different wavelengths, as described in more detail below.

The controller 60 includes a synchronizer 72 that synchronizes the measurement signal 68 with the monitor signal 70. Together the measurement detector 52, the monitor detector 105, and a synchronizer 72 implement a "signal normalization subsystem." The signal normalization subsystem normalizes the measurement signal to compensate for fluctuations in the illuminating light 102. For example, in one implementation the synchronizer 72 buffers samples of both signals (e.g., from analog-to-digital converters) and outputs the samples of one signal delayed with respect to samples of the other signal by a programmable time delay value. This synchronization enforces a phase relationship between the signals.

Since the measurement detector 52 and the monitor detector 105 are synchronized with respect to each other, fluctuations in the illuminating light 102 appear in both the measurement signal 68 and the monitor signal 70 at approximately the same time. The controller 60 divides the measurement signal 68 by the monitor signal 70 to provide a compensated measurement signal from which the controller 60 can obtain the imaging and/or spectral information. In some cases, the measurement signal 68 and the monitor signal 70 are obtained by integrating a fluctuating signal over a measurement time period. In these cases, the controller 60 uses the signal normalization subsystem to compensate for averaged signal fluctuations that remain after the integration.

Other techniques can also be used to compensate for fluctuations in the illuminating light 102. For example, various forms of feedback to the light source 100 can provide signal normalization including: variable injection current; variable cavity loss with a polarizer, acousto-optic cell, electro-optic cell, or spatial light modulator; or a variable reflectivity output coupler.

2 Light Source

The light source 100 includes an optical cavity (or "optical resonator") for providing low-coherence light. Before describing particular examples of optical cavities configured to provide such low-coherence light, it is helpful to describe some properties of optical cavities. An optical cavity defines a round-trip path (e.g., defined by two or more reflectors) whose length $L_{rt}$ defines a set of longitudinal modes of light circulating in the optical cavity. Each longitudinal mode has a corresponding peak optical frequency (or equivalently, a peak optical wavelength).

Figure 2:
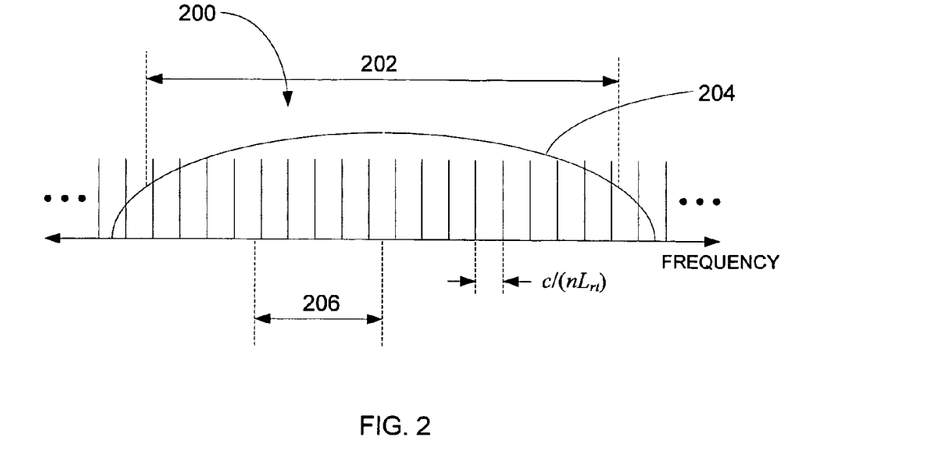
FIG. 2 is a plot showing longitudinal mode peak frequencies for an optical cavity and a gain profile for a gain medium in the optical cavity.

FIG. 2 shows a plot of these peak frequencies 200. The "mode spacing" between these peak optical frequencies is given by $c/(nL_{rt})$ where c is the speed of light in a vacuum and n is the average refractive index along the round-trip path. The "optical length" of the optical cavity is given by $nL_{rt}$.

Each longitudinal mode also has a linewidth determined mainly by the round-trip loss in the optical cavity. Light corresponding to a given longitudinal mode will have a spectrum defined by the linewidth of that mode. Larger round-trip loss corresponds to a broader linewidth.

The optical cavity also includes a gain medium. The gain medium provides gain for a subset of the longitudinal modes that fall within a gain band 202 defined by the gain medium. For example, one definition of the gain band is the band of frequencies over which the gain profile 204 is above half of its maximum value, also called the Full-Width Half-Maximum (FWHM) band. When the gain medium is pumped at an operative level, one or more longitudinal modes within the gain band will experience enough gain in a round trip to overcome the round-trip loss. These modes will oscillate (or "lase"), causing light at the corresponding peak wavelength to be emitted from the optical cavity.

In the case of a gain medium that provides gain through population inversion, the gain medium can be "homogeneously broadened" or "inhomogeneously broadened." In the homogeneously broadened case, there exists competition among the longitudinal modes within the gain band, such that only that longitudinal mode experiencing the most net gain (i.e., gain in excess of loss) will oscillate. In the inhomogeneously broadened case, multiple longitudinal modes within the gain band (and potentially outside of the gain band if the medium is pumped strongly enough) can oscillate at the same time. This spectral band 206 over which these longitudinal modes oscillate is called the "oscillation band." Since the round-trip loss may not be uniform across the gain band 202, the oscillation band 206 may not be aligned with the center of the gain band 202. In some implementations, the optical cavity incorporates a tuning element to shift the oscillation band 206 relative to the gain band 202.

A larger value of the optical length $nL_{rt}$ yields a smaller mode spacing $c/(nL_{rt})$, and therefore more longitudinal modes falling within the gain band 202. The optical length $nL_{rt}$ of the optical cavity thus influences how many longitudinal modes can potentially oscillate.

The increasing density of modes caused by a large optical length can cause temporal effects that can be detected by some systems that use the light. One such temporal effect is mode-beating between longitudinal modes that have close to the same frequency. High-frequency mode-beating may not cause temporal effects (e.g., power fluctuations in a detected signal) if the beat frequency is outside the detection range of the system (e.g., detection bandwidth and/or integration bandwidth).

Another temporal effect that can be caused by large optical length is reduction in coherence time (or equivalently, temporal coherence length) due to any of a variety of nonlinear effects including low-frequency fluctuations, high-frequency chaotic oscillations and other types of multimode laser dynamics. In some cases, this reduced temporal coherence length is useful to reduce speckle that can cause noise in a detected signal. Depending on the characteristics of the optical cavity and the gain medium, the round-trip optical length of the cavity needed to sufficiently reduce the temporal coherence length may be as large as 10 meters, 50 meters, 100 meters, or 500 meters.

To induce some of these temporal effects, the optical length of an optical cavity can be increased by incorporating into the optical cavity an optical waveguide. The stability of an optical cavity depends upon the existence of a supported spatial mode profile within the optical cavity. An optical waveguide inside an optical cavity can be made long enough to reduce the temporal coherence length without causing the cavity to be unstable since the length of a waveguide does not necessarily change the spatial mode profile that it supports. For example, an optical fiber inside an optical cavity can increase the optical length by tens or hundreds of meters or more, as necessary to induce the desired temporal effects.

The light source 100 incorporates these techniques to provide low-coherence radiation to the spectroscopic catheter system 50. For example, the length of the optical fiber is selected to cause a temporal coherence length of light emitted from an optical cavity in the light source 100 to be shorter than a scattering distance associated with the target area 22 (or other sample being analyzed by the system 50). Even though the resulting low-coherence light may have significant spectral content, since the spectral features to be scanned are typically relatively wide and diffuse, the system 50 still has sufficient spectral resolution for collecting the desired spectral information.

3 Optical Cavity Configurations

Figure 3A:
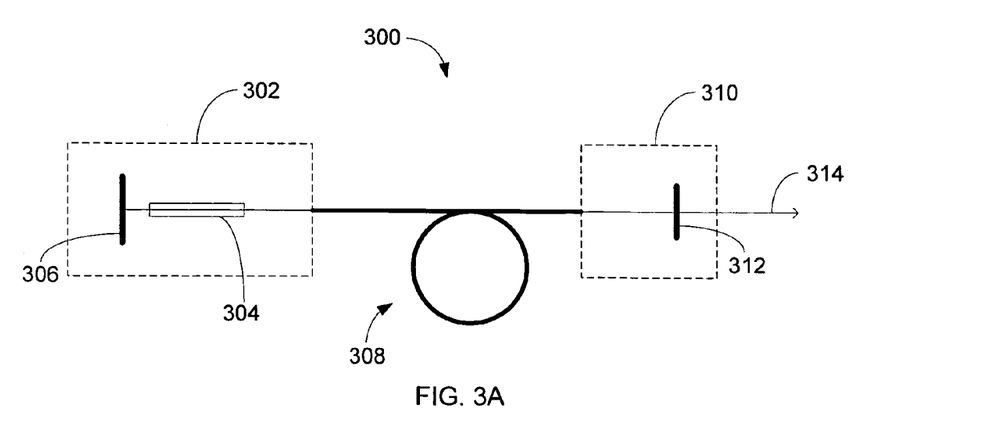
FIGS. 3A-3C and 4A-4C are schematic diagrams of optical cavity configurations.

FIG. 3A shows a general configuration of an optical cavity 300 used in an implementation of the light source 100. The optical cavity 300 includes an optical gain module 302 that includes a gain medium 304 and a first reflector 306. An optical fiber 308 couples light between the optical gain module 302 and an optical feedback element 310. The optical feedback element 310 includes a second reflector 312 that reflects light back through the optical fiber 308 to the optical gain module 302, forming a round-trip path. In this configuration, light 314 is coupled out of the optical cavity 300 through the optical feedback element 310. Alternatively, light can be coupled out of the optical cavity 300 from any location, including from the optical fiber 308 (e.g., using a multiport fiber coupler). In some implementations, the optical feedback element 310 includes a frequency selective element for tuning the spectrum of the output radiation 314.

Figure 3B:
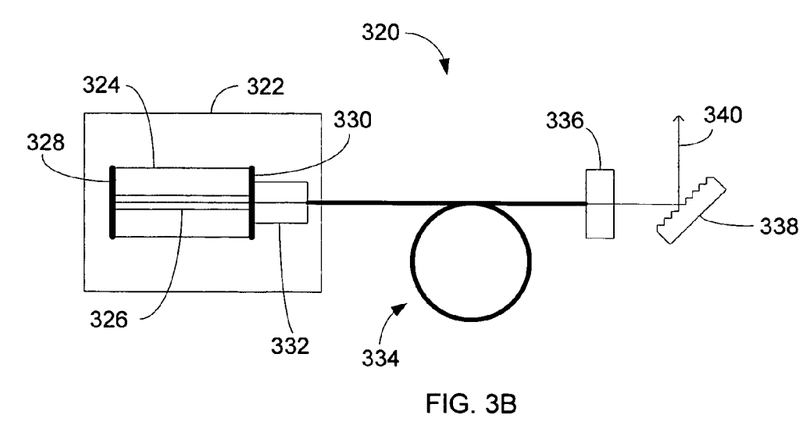

FIG. 3B shows an exemplary optical cavity 320 configured according to a Littrow configuration. The optical cavity 320 includes a semiconductor opto-electronic module 322 as an optical gain module. The module 322 includes a semiconductor chip 324, such as a semiconductor optical amplifier (SOA) chip. The semiconductor chip includes a gain waveguide 326 that provides gain in response to a pump current provided by the module 322. The back facet of the semiconductor chip 324 has a highly reflective (HR) coating 328. The front facet of the semiconductor chip 324 has an anti-reflective (AR) coating 330. The AR coating 330 reduces optical feedback into the semiconductor chip 324, allowing reflector external to the module 322 to provide the optical feedback needed for oscillation.

A first spatial mode coupler 332 couples light from the gain waveguide 326 to an optical fiber 334. In one embodiment, this is achieved by providing an optical fiber 334 having a fiber "pigtail," such as a single mode fiber, that extends through a fiber feed-through in a hermetic package of the module 322. The optical fiber 334 can include a single span of optical fiber, or multiple spans of optical fiber spliced or coupled together, yielding a total optical fiber of any desired length. In other implementations, a double pigtailed SOA chip can be used. In these implementations, a back reflector is provided by a fiber Bragg grating formed in one of the pigtails or by cleaving one of the pigtails to form a flat facet and applying an HR coating to the facet. In other implementations, the gain medium can be provided in a doped portion of the optical fiber 334.

Some techniques for coupling light from the gain waveguide 326 to the optical fiber 334 include aspects that prevent instabilities from "stray" or "unwanted" cavities formed by reflections from different optical components.

For example, the AR coating 330 reduces unwanted reflections, however, the bandwidth of the AR coating 330 can limit the usable bandwidth of a given semiconductor gain medium. In some implementations the gain waveguide 326 is butt-coupled to the optical fiber 334. Since the difference in refractive index between the gain waveguide 326 and the optical fiber 334 is smaller than difference in refractive index between the gain waveguide 326 and air, an AR coating in between the gain waveguide 326 and the optical fiber 334 can be designed to have a broader bandwidth.

In some implementations in which light is coupled into or out of the optical fiber 334 through air, one or both end facets are polished at an angle (e.g., 8 degrees) to reduce unwanted back-reflections at the facets. A Brewster's angle polish can be used to reduce the reflection from that the facet essentially to zero.

Additionally, in some implementations the optical fiber 334 is a polarization-maintaining fiber.

In determining the optical length of the optical cavity 320, both the actual physical length of the optical fiber 334 and its index of refraction are considered. Thus, a 70-meter span of fiber with an index of refraction of 1.4 increases the optical length of the cavity 320 by about 100 meters.

A second spatial mode coupler 336 couples light from the optical fiber 334 to a diffraction grating 338 (or other frequency selective tunable element such as a stretchable fiber Bragg grating, a fiber on an electro-optic tuning element, a Fabry Perot filter, a tilted dielectric stack mirror, etc.) via free space transmission. The second spatial mode coupler 336 can include, for example, a collimating lens to collect a diverging beam from the tip of the optical fiber 334 and a cylindrical lens to shape the spot of the incident beam at the diffraction grating 338. The diffraction grating 338 reflects a portion of the first order diffracted beam back into the optical fiber 334 to provide frequency selective optical feedback to the semiconductor chip 324 thereby determining which modes will oscillate.

The location of the oscillation band 206 relative to the gain band 202 (see FIG. 2) depends on the incident angle of the beam at the diffraction grating. The extent of the oscillation band 206 is based on the resolving power of the diffraction grating 338, which in turn depends on the grating pitch, the spot size of the incident beam, and the incident angle. As a result, grating properties such as pitch can be selected along with cavity length to determine the number of longitudinal modes that oscillate and the resulting temporal properties of the illuminating light 102. In one implementation, the diffraction grating 338 is a 600 line/millimeter (mm) diffraction grating, which is 12×12×6 mm in size. (A suitable grating is that sold by Optometrics, LLC of Ayer, MA as Part No. 3-4669).

The diffraction grating 338 provides tunable feedback into the semiconductor chip 324. The diffraction grating 338 is angle tuned under the control of the controller 60 to scan the oscillation band 206 relative to the gain band 202 and thus control the spectrum of the illuminating light 102. In one implementation, the angle of the diffraction grating 338 is controlled using a resonant galvanometer. The galvanometer is tuned to scan the spectrum relatively quickly, for example, in less than 50 milliseconds, to remove motion artifacts due to the beating of the heart. In other implementations, other types of frequency selective tunable elements are used. For example, acousto-optic filters and Bragg gratings can be used in place of the diffraction grating 338.

That portion of the output of the optical cavity 320 that forms the illuminating light 102 for the catheter 56 can be coupled from any convenient location in the optical cavity 320. In some embodiments, the zeroth order diffracted beam 340 provides the illuminating light 102. Alternatively, a three-port tap device coupled to the optical fiber 334 provides the illuminating light 102.

Figure 3C:
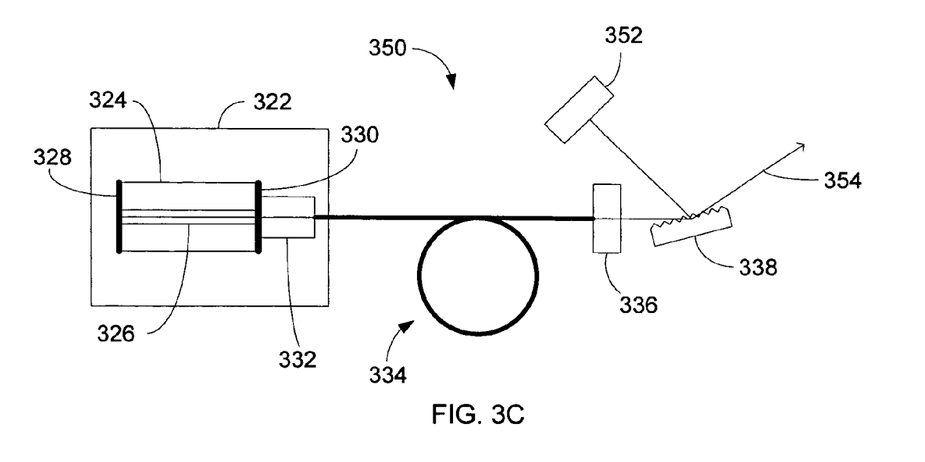

FIG. 3C shows an exemplary optical cavity 350 configured according to a Littman-Metcalf configuration. The Littman-Metcalf optical cavity 350 includes elements 322-338 as described above for the Littrow optical cavity 320. Additionally, the optical cavity 350 includes a reflector 352 (e.g., a mirror or a prism retro-reflector) that reflects a portion of the first order diffracted beam back into the optical fiber 334. In this configuration, the reflector 352 can be used to tune the spectrum of the illuminating light 102 without changing the angle of the zeroth order diffracted beam 354.

In some implementations, the light source 100 includes multiple gain media to provide, for example, increased power, wider tuning ranges from multiple tunable sources, or multiple wavelengths from multiple non-tunable sources. Light from two or more optical cavities can be coupled internally to at least one of the optical cavities (using "intra-cavity" coupling) or externally to the optical cavities.

In some implementations, the cavity configuration includes features to reduce noise such as amplified spontaneous emission (ASE) noise as described in U.S. Pat. No. 6,608,847 or U.S. Pat. No. 6,788,726, each of which is incorporated herein by reference.

Any of a variety of approaches can be used to couple light from multiple gain media, either inside (internally) or outside (externally) any of the respective cavities. One approach uses a power combiner or beam splitter. Another approach uses a polarizing beam combiner to take advantage of the different states of polarization from two different gain media. Another approach uses a frequency selective or wavelength division multiplexing (WDM) filter to combine the beams from the gain media. Another approach uses a switch to switch among beams from various gain media.

A variety of types of gain media can be used in any of these cavity configurations including semiconductor materials such as InP, InAs, and InGaAs. Other types of gain media include, for example, doped crystals such as Ti:Saphire, BBO, Nd:Glass, Nd:YAG, Cr:YAG, Cr:forsterite, and Cr:gehlenite.

Figure 4A:
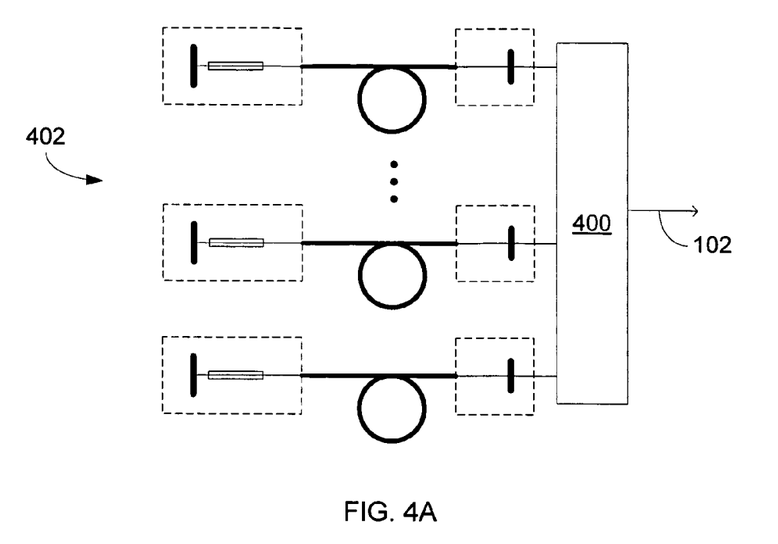

FIG. 4A shows an external coupling architecture. A switch 400 selects light from an array 402 of optical cavities (either tunable or non-tunable). The source 100 can switch among the optical cavities (e.g., in a round-robin order) to provide the illuminating light 102, effectively scanning the source spectrum to probe the NIR spectral response of the target area 22, even if each individual optical cavity is non-tunable.

Exemplary architectures for intra-cavity coupling of two or more gain media can be divided into two classes: serial and parallel.

In serial architectures, two or more gain media, with offset gain bands, are present in an optical cavity. A frequency selective element, such as a grating, is tuned first across a first wavelength range of the first gain medium, then tuned across a second wavelength range of the second gain medium, and so forth depending on the number of addition gain media that are present. Thus, the spectrum of the output light tunes in a serial fashion.

In parallel architectures, light from multiple gain media is combined, and a frequency selective element is tuned such that both gain media receive feedback simultaneously and in parallel. Thus, multiple spectral lasing peaks will appear at the output. As the frequency selective element is tuned these peaks will be scanned simultaneously, allowing access to multiple wavelength regions. Approaches for combining light from the gain media include using a frequency selective mirror (WDM), and offsetting the angle of incidence of the light sources on a diffraction grating.

These serial and parallel architectures are described in more detail in U.S. patent application Ser. No. 10/259,076 (Publication No. U.S. 2004/064022), incorporated herein by reference.

Figure 4B:
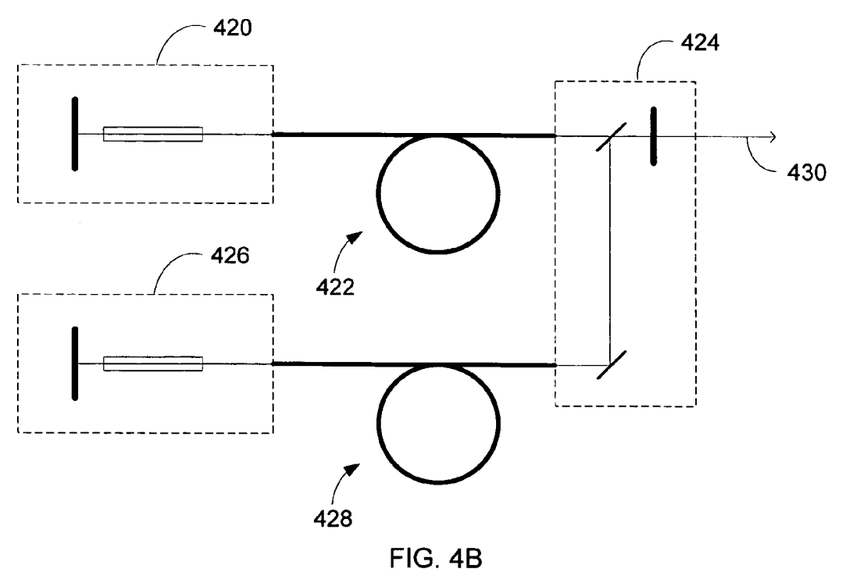

FIG. 4B shows a first exemplary optical cavity configuration for intra-cavity beam combining in which a first optical gain module 420 couples to a multi-port optical feedback element 424 via a first optical fiber 422. A second optical gain module 426 is coupled to the multi-port optical feedback element 424 via a second optical fiber 428. The multi-port optical feedback element 424 receives input light over multiple input ports and provides optical feedback to both optical gain modules (at their respective optical inputs). The first and second optical fibers 422, 428 are each long enough to cause the temporal coherence length of output light 430 to be shorter than a scattering distance associated with the target area 22, in this case, a mean free path within a scattering medium between the catheter head 58 and the target area 22.

Figure 4C:
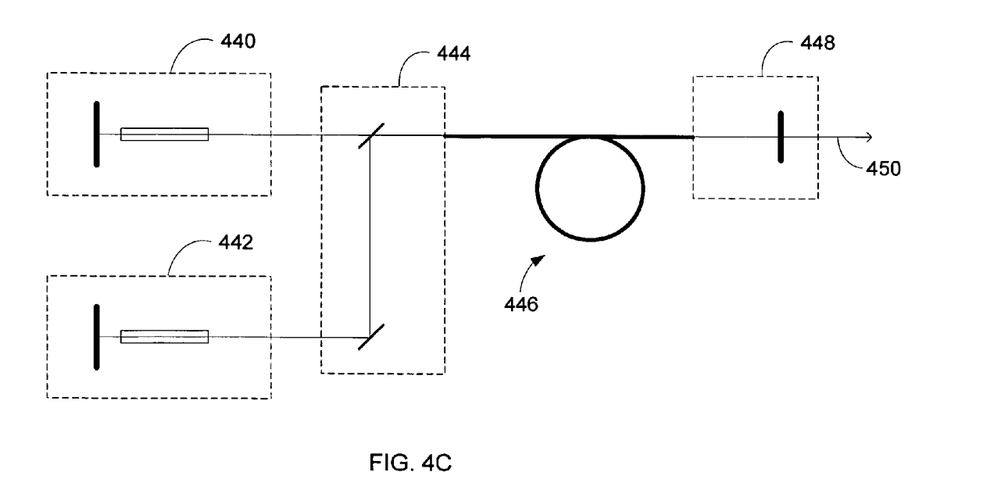

FIG. 4C shows a second exemplary optical cavity configuration for intra-cavity beam combining. A first optical gain module 440 and a second optical gain module 442 couple to a multi-port optical coupler 444 (e.g., by free-space propagation or by an optical fiber). In this configuration, a single optical fiber 446 couples light from both optical gain modules to an optical feedback element 448. The length of this optical fiber 446 is long enough to cause the temporal coherence length of output light 450 to be shorter than a mean free path within a scattering medium between the catheter head 58 and the target area 22.

Other embodiments are within the scope of the following claims. The techniques for providing low-coherence light can be combined with any of a variety of other techniques including, for example, techniques for controlling transverse spatial modes in an optical cavity as described in more detail in U.S. application Ser. No. 10/683,979 (Publication No. 2004/0136433), incorporated herein by reference. The techniques for providing low-coherence light can also be used in any of a variety of environments for a variety of applications. For example, in addition to medical applications, low-coherence light is useful in applications in which laser light illuminates a target area, such as laser projectors illuminating rough surfaces or screens.

What is claimed is:

1. An apparatus for illuminating a target area, the apparatus comprising:
   reflectors defining a first optical cavity, the first optical cavity defining a first set of longitudinal modes;
   a first gain medium defining a first gain band, the first gain medium configured to cause a plurality of the longitudinal modes of the first set to oscillate over an oscillation band within the first gain band when the first gain medium is pumped at an operative level; and
   a first optical waveguide positioned within the first optical cavity, the first optical waveguide having a length selected to cause a temporal coherence length of light emitted from the first optical cavity to be shorter than a scattering distance associated with the target area.

2. The apparatus of claim 1, wherein the scattering distance comprises a mean free path within the scattering medium adjacent to the target area.

3. The apparatus of claim 1, wherein the scattering distance comprises a transverse roughness of the target area.

4. The apparatus of claim 1, further comprising:
   a signal normalization system configured to detect intensity fluctuations in light emitted from the first optical cavity and to normalize, at least in part on the basis of the detected intensity fluctuations, a signal derived from light scattered from the target area.

5. The apparatus of claim 4, wherein the signal normalization system comprises:
   a first detector positioned to detect a portion of the light emitted from the first optical cavity; and
   a second detector positioned to detect the light scattered from the target area.

6. The apparatus of claim 5, wherein the signal normalization system further comprises a synchronizer configured to enforce a phase relationship between a signal generated by the first detector and a signal generated by the second detector.

7. The apparatus of claim 1, wherein the first gain medium comprises a semiconductor material.

8. The apparatus of claim 1, wherein the first gain medium comprises a doped crystal.

9. The apparatus of claim 1, further comprising:
   a tuning element, positioned within the first optical cavity, that causes the oscillation band to shift relative to the gain band in response to a control signal.

10. The apparatus of claim 9, wherein the tuning element is selected from the group consisting of a diffraction grating, a stretchable fiber Bragg grating, a fiber on an electro-optic tuning element, a Fabry Perot filter, and a tilted dielectric stack mirror.

11. The apparatus of claim 1, further comprising:
    reflectors defining a second optical cavity, the second optical cavity defining a second set of longitudinal modes;
    a second gain medium defining a second gain band, the second gain medium configured to cause a plurality of the longitudinal modes of the second set to oscillate over an oscillation band within the second gain band when the second gain medium is pumped at an operative level
    a coupling element configured to couple light from the first optical cavity with light from the second optical cavity.

12. The apparatus of claim 11, wherein the coupling element couples light from the first and second optical cavities inside at least one of the first and second optical cavities.

13. The apparatus of claim 11, wherein the coupling element couples light from the first and second optical cavities outside the first and second optical cavities.

14. The apparatus of claim 11, further comprising:
a second optical waveguide positioned within the second optical cavity, the second optical waveguide having a length selected to cause a temporal coherence length of light emitted from the second optical cavity to be shorter than a scattering distance associated with the target area.

15. The apparatus of claim 1, further comprising:
a catheter in optical communication with the first optical cavity, the catheter being configured to deliver light from the first optical cavity to the target area through the scattering medium and to collect scattered light from the target area.

16. The apparatus of claim 15, further comprising:
a spectrum analyzer in optical communication with the catheter, the spectrum analyzer being configured to receive the scattered light.

17. The apparatus of claim 1, wherein a round-trip optical length of the first optical cavity is longer than 10 meters.

18. The apparatus of claim 17, wherein the round-trip optical length of the first optical cavity is longer than 50 meters.

19. The apparatus of claim 18, wherein the round-trip optical length of the first optical cavity is longer than 100 meters.

20. The apparatus of claim 19, wherein the round-trip optical length of the first optical cavity is longer than 500 meters.

21. The apparatus of claim 1 wherein the first optical cavity is configured according to a Littrow configuration.

22. The apparatus of claim 1 wherein the first optical cavity is configured according to a Littman-Metcalf configuration.

23. A method for illuminating a target area, the method comprising:
providing reflectors defining an optical cavity, the optical cavity defining a set of longitudinal modes;
pumping a gain medium within the optical cavity at an operative level to cause a plurality of the longitudinal modes of the set to oscillate over an oscillation band within a gain band defined by the gain medium; and
positioning an optical waveguide within the optical cavity, the optical waveguide having a length selected to cause a temporal coherence length of light emitted from the optical cavity to be shorter than a scattering distance associated with the target area.

24. The method of claim 23, further comprising:
detecting intensity fluctuations in light emitted from the optical cavity; and
normalizing, at least in part on the basis of the detected intensity fluctuations, a signal derived from light scattered from the target area.

* * * * *